US008191168B2

(12) United States Patent
Man et al.

(10) Patent No.: US 8,191,168 B2
(45) Date of Patent: May 29, 2012

(54) METHOD OF PREPARING A TRANSMISSION ELECTRON MICROSCOPE SAMPLE AND A SAMPLE PIECE FOR A TRANSMISSION ELECTRON MICROSCOPE

(75) Inventors: Xin Man, Chiba (JP); Kouji Iwasaki, Chiba (JP); Tatsuya Asahata, Chiba (JP)

(73) Assignee: SII NanoTechnology Inc., Chiba (JP)

(*) Notice: Subject to any disclaimer, the term of this patent is extended or adjusted under 35 U.S.C. 154(b) by 423 days.

(21) Appl. No.: 12/264,750

(22) Filed: Nov. 4, 2008

(65) Prior Publication Data

US 2009/0119807 A1    May 7, 2009

(30) Foreign Application Priority Data

Nov. 6, 2007   (JP) ................................. 2007-288292
Oct. 21, 2008   (JP) ................................. 2008-270964

(51) Int. Cl.
*G01N 13/10* (2006.01)

(52) U.S. Cl. .................... 850/18; 850/5; 850/8; 850/63; 250/306; 250/310; 250/311; 250/440.11; 250/442.11; 73/863

(58) Field of Classification Search .................... None
See application file for complete search history.

(56) References Cited

U.S. PATENT DOCUMENTS

| | | | | |
|---|---|---|---|---|
| 5,270,552 A | * | 12/1993 | Ohnishi et al. | 250/307 |
| 5,656,811 A | * | 8/1997 | Itoh et al. | 850/43 |
| 6,188,068 B1 | * | 2/2001 | Shaapur et al. | 850/8 |
| 6,538,254 B1 | * | 3/2003 | Tomimatsu et al. | 250/442.11 |
| 6,627,889 B2 | * | 9/2003 | Ochiai et al. | 850/9 |
| 6,717,156 B2 | * | 4/2004 | Sugaya et al. | 250/440.11 |
| 7,372,050 B2 | * | 5/2008 | Fukuda et al. | 250/492.21 |
| 7,375,325 B2 | * | 5/2008 | Burkhardt et al. | 250/307 |
| 2002/0005492 A1 | * | 1/2002 | Hashikawa et al. | 250/442.11 |
| 2002/0166976 A1 | * | 11/2002 | Sugaya et al. | 250/440.11 |
| 2003/0089852 A1 | * | 5/2003 | Ochiai et al. | 250/310 |
| 2003/0089860 A1 | * | 5/2003 | Asjes | 250/442.11 |
| 2004/0245464 A1 | * | 12/2004 | Iwasaki et al. | 250/307 |
| 2006/0010968 A1 | * | 1/2006 | Munekane et al. | 73/104 |
| 2006/0011868 A1 | * | 1/2006 | Kidron et al. | 250/492.22 |
| 2006/0261270 A1 | * | 11/2006 | Burkhardt et al. | 250/311 |
| 2010/0032581 A1 | * | 2/2010 | Sugaya et al. | 250/442.11 |

FOREIGN PATENT DOCUMENTS

JP    2006-120391 A    5/2006

* cited by examiner

*Primary Examiner* — Michael Logie
(74) *Attorney, Agent, or Firm* — Brinks Hofer Gilson & Lione (57) ABSTRACT

Provided is a method of preparing a sample piece for a transmission electron microscope, the sample piece for a transmission electron microscope including a substantially planar finished surface which can be observed with the transmission electron microscope and a grabbing portion which microtweezers can grab without contacting the finished surface. The method of preparing a sample piece for a transmission electron microscope is characterized by including: a first step of cutting out the sample piece from a sample body Wa with a charged particle beam, the sample piece being coupled to the sample body at a coupling portion; a second step of grabbing with the microtweezers the grabbing portion of the sample piece with the finished surface of the sample piece cut out in the first step being covered with the microtweezers; a third step of detaching the sample piece grabbed with the microtweezers in the second step from the sample body by cutting the coupling portion with the charged particle beam with a grabbed state of the sample piece being maintained; and a fourth step of transferring and fixing with the microtweezers the sample piece detached in the third step onto a sample holder.

5 Claims, 10 Drawing Sheets

FIG. 18

METHOD OF PREPARING A TRANSMISSION ELECTRON MICROSCOPE SAMPLE AND A SAMPLE PIECE FOR A TRANSMISSION ELECTRON MICROSCOPE

RELATED APPLICATIONS

This application claims priority under 35 U.S.C. §119 to Japanese Patent Application Nos. JP2007-288292 filed on Nov. 6, 2007 and JP2008-270964 filed on Oct. 21, 2008, the entire contents of which are hereby incorporated by reference.

BACKGROUND OF THE INVENTION

The present invention relates to a method of preparing a transmission electron microscope sample using a charged particle beam and a sample piece for a transmission electron microscope obtained as a result of the preparation method.

Conventionally, for the purpose of observing a sample with a transmission electron microscope (TEM), a sample piece for a transmission electron microscope (hereinafter, simply referred to as sample piece) is prepared using a focused ion beam (FIB, a kind of charged particle beam) system (see, for example, JP 2006-120391 A).

In a conventional sample preparation method using a focused ion beam system, a sample piece is first cut out from an original sample body with a focused ion beam, and is then grabbed by grabbing means provided to the focused ion beam system and detached from the sample body. Then, while being grabbed by the grabbing means, the sample piece is transferred to a sample holder to be fixed thereto, and is finish-processed on the sample holder such that a finished surface which can be observed with a transmission electron microscope is obtained.

In the above-mentioned sample preparation method, the focused ion beam is used not only for the purpose of processing the sample but also for the purpose of observing the sample midway through the processing. Specifically, secondary charged particles generated when the sample is irradiated with the focused ion beam are detected by a detector provided in the focused ion beam system. By converting the detected secondary charged particles into a luminance signal or the like, an image of the sample is displayed on a display portion provided to the focused ion beam system.

However, the method of preparing a transmission electron microscope sample described in Patent Document 1 has a problem in that the finished surface can not be processed with the sample piece being coupled to the sample body. Specifically, if the finished surface is processed with the sample piece being coupled to the sample body, contamination is generated on a surface of the sample piece under the influence of the charged particle beam used when the sample piece is detached from the sample body. If a sample piece with a large amount of contamination generated thereon is observed as it is with a transmission electron microscope, the quality of the observed image is adversely affected, and thus, it is difficult to process the finished surface so as to be observable with a transmission electron microscope with the sample piece being coupled to the sample body.

Therefore, in the conventional method, with the sample piece being coupled to the sample body, only rough processing as a stage before processing of forming the finished surface is carried out, and the processing of forming the finished surface is carried out after the sample piece is fixed onto the sample holder. Specifically, after the sample piece is fixed onto the sample holder, the finished surface is processed again with a charged particle beam, which decreases the productivity.

The present invention is made in view of the above-mentioned circumstance, and therefore provides a method of preparing a transmission electron microscope sample and a sample piece for a transmission electron microscope with increased productivity.

SUMMARY OF THE INVENTION

In order to solve the above-mentioned problem, the present invention proposes the following means.

The present invention provides a method of preparing a transmission electron microscope sample for detaching with a charged particle beam a sample piece for a transmission electron microscope from a sample body, the sample piece for a transmission electron microscope including a substantially planar finished surface which can be observed with a transmission electron microscope and a grabbing portion which microtweezers can grab without contacting the finished surface, and for transferring the sample piece for a transmission electron microscope with the microtweezers to fix the sample piece for a transmission electron microscope onto a sample holder, the method being characterized by including: a first step of cutting out the sample piece for a transmission electron microscope from the sample body with the charged particle beam with a coupling portion for coupling the sample piece for a transmission electron microscope to the sample body remaining; a second step of grabbing with the microtweezers the grabbing portion of the sample piece for a transmission electron microscope with the finished surface of the sample piece for a transmission electron microscope cut out in the first step being covered with the microtweezers; a third step of detaching the sample piece for a transmission electron microscope grabbed with the microtweezers in the second step from the sample body by cutting the coupling portion with the charged particle beam with a grabbed state of the sample piece for a transmission electron microscope being maintained; and a fourth step of grabbing with the microtweezers the sample piece for a transmission electron microscope detached in the third step to transfer and fix the sample piece for a transmission electron microscope onto the sample holder.

It is to be noted that the microtweezers refer to means which is controlled by a control portion provided in a charged particle beam system and which can grab, cover, and transfer the sample piece for a transmission electron microscope in the charged particle beam system.

In the method of preparing a transmission electron microscope sample according to the present invention, because the finished surface of the sample piece for a transmission electron microscope is covered in the second step, contamination of the finished surface by the charged particle beam used when the coupling portion is cut in the third step can be prevented. This makes it possible to process the finished surface with the sample piece for a transmission electron microscope being coupled to the sample body, and therefore, productivity in preparing the sample piece for a transmission electron microscope can be increased.

Further, in the first step, the grabbing portion of the sample piece for a transmission electron microscope is preferably processed such that a thickness of the grabbing portion is larger than a thickness of the finished surface.

In the method of preparing a transmission electron microscope sample according to the present invention, because the grabbing portion is thicker than the finished surface, when the grabbing portion is grabbed in the second step, the microtweezers do not contact the finished surface. This prevents the finished surface from being damaged even when the sample piece for a transmission electron microscope is grabbed with the finished surface covered with the microtweezers.

Further, in the first step, after the grabbing portion of the sample piece for a transmission electron microscope is cut out, the finished surface of the sample piece for a transmission electron microscope is preferably processed.

In the method of preparing a transmission electron microscope sample according to the present invention, because, in the first step, the grabbing portion is processed and then the finished surface is processed, a period of time during which the finished surface is irradiated with the charged particle beam can be shortened. This makes it possible to suppress contamination of the finished surface.

Further, the present invention provides a sample preparation method of detaching with a charged particle beam a sample piece for a transmission electron microscope from a sample body, the sample piece for a transmission electron microscope including a substantially planar finished surface which can be observed with a transmission electron microscope and a grabbing portion which microtweezers can grab without contacting the finished surface, and for transferring the sample piece for a transmission electron microscope with the microtweezers to fix the sample piece for a transmission electron microscope onto a sample holder, the sample preparation method being characterized by including: a first step of forming a thin piece portion including the grabbing portion and the finished surface by etching the sample body using the charged particle beam with a coupling portion for coupling the thin piece portion to the sample body remaining; a second step of grabbing with the microtweezers the grabbing portion of the sample piece for a transmission electron microscope with the finished surface of the thin piece portion formed in the first step being covered with the microtweezers; a third step of detaching the thin piece portion grabbed with the microtweezers in the second step from the sample body by cutting the coupling portion with the charged particle beam with a grabbed state of the thin piece portion being maintained to form the sample piece for a transmission electron microscope; and a fourth step of grabbing with the microtweezers the sample piece for a transmission electron microscope detached in the third step to transfer and fix the sample piece for a transmission electron microscope onto the sample holder.

In the method of preparing a transmission electron microscope sample according to the present invention, because the finished surface of the thin piece portion is covered in the second step, contamination of the finished surface by the charged particle beam used when the coupling portion is cut in the third step can be prevented. This makes it possible to process the finished surface with the sample piece for a transmission electron microscope being coupled to the sample body, and therefore, productivity in preparing the sample piece for a transmission electron microscope can be increased.

Further, the present invention provides a sample piece for a transmission electron microscope detached from a sample body to be made available as an object to be observed with a transmission electron microscope, characterized by including: a substantially planar finished surface which can be observed with the transmission electron microscope; and a grabbing portion having a thickness set to be larger than a thickness of the finished surface. The finished surface and the grabbing portion are processed before the sample piece for a transmission electron microscope is detached from the sample body.

The sample piece for a transmission electron microscope according to the present invention has an action and an effect similar to those in the above-mentioned case of Claim 2.

In the method of preparing a transmission electron microscope sample using the charged particle beam and the sample piece obtained as a result of the preparation method according to the present invention, when the sample piece is irradiated with the charged particle beam to be detached from the sample body, by covering the finished surface of the sample piece from the charged particle beam, the finished surface can be processed with the sample piece being coupled to the sample body. Because it is not necessary to process again the finished surface after the sample piece is fixed onto the sample holder, a method of preparing a transmission electron microscope sample and a sample piece for a transmission electron microscope with increased productivity can be provided.

DETAILED DESCRIPTION OF THE PREFERRED EMBODIMENT

Figure 1:
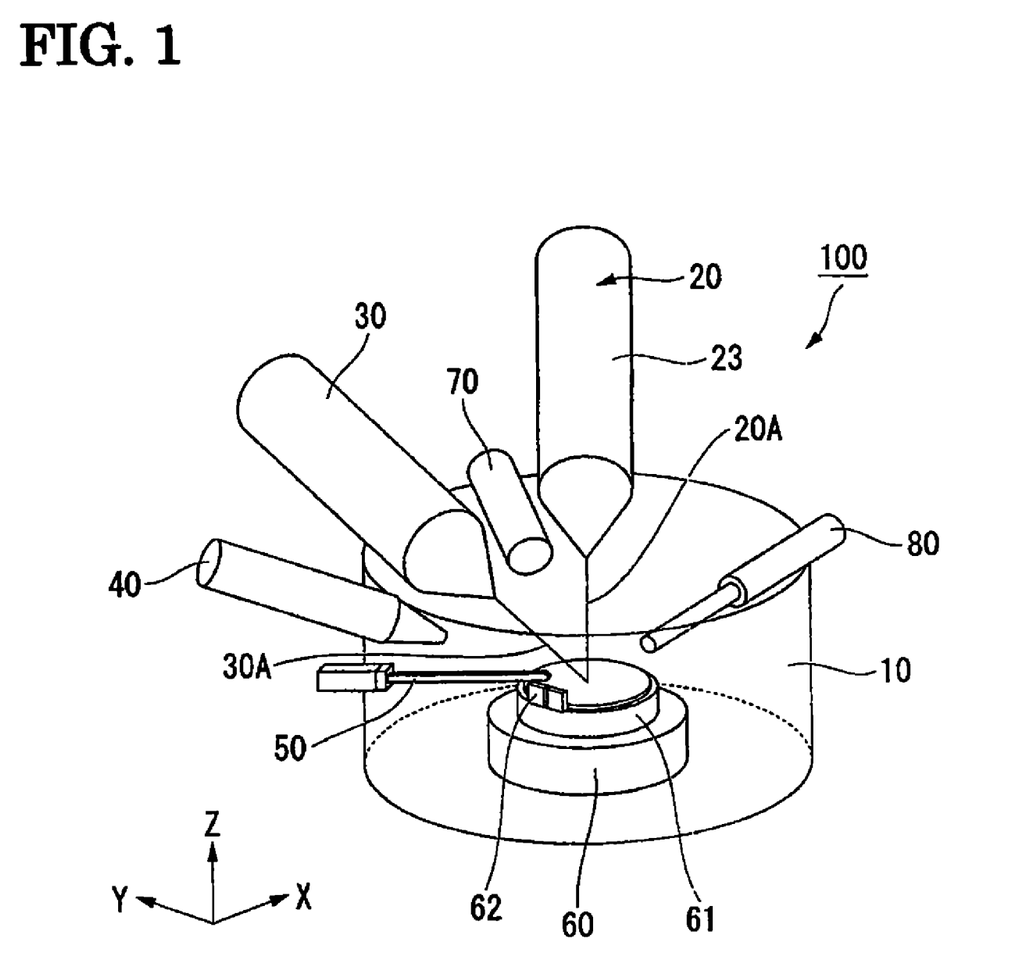
FIG. 1 shows a schematic perspective view of a charged particle beam system used in an embodiment of the present invention.
Figure 2:
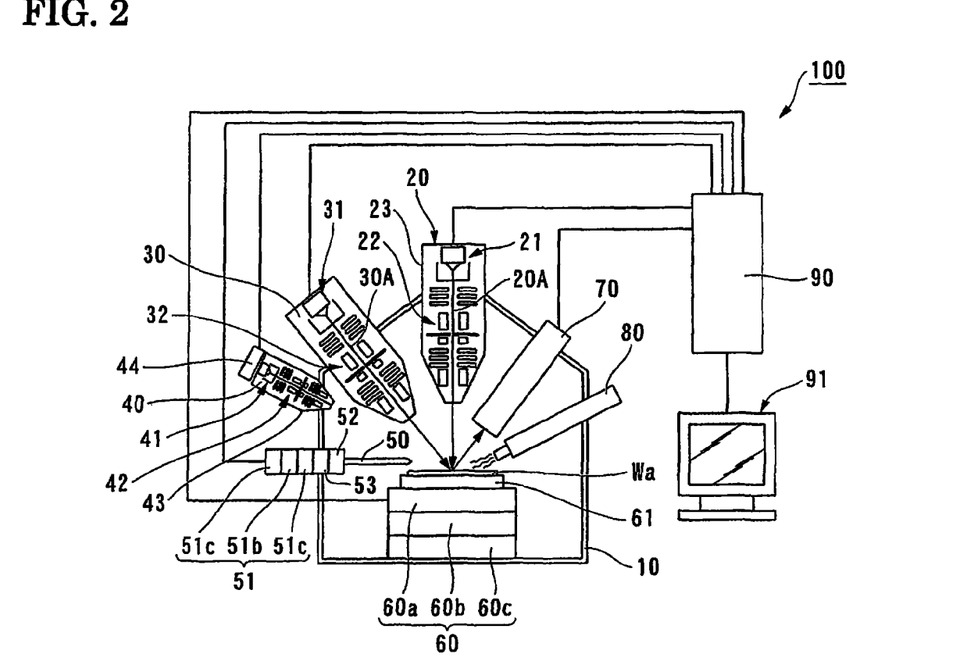
FIG. 2 shows a schematic sectional view of the charged particle beam system used in the embodiment of the present invention.

An embodiment of a method of preparing a transmission electron microscope sample according to the present invention is described in the following with reference to the drawings. Before describing the method of preparing a transmission electron microscope sample according to the present invention, a charged particle beam system directly used in carrying out the method is described. FIG. 1 is a schematic perspective view of a charged particle beam system 100. FIG. 2 is a schematic sectional view of the charged particle beam system 100.

As illustrated in FIG. 1 and FIG. 2, the charged particle beam system 100 includes a vacuum chamber 10, an ion beam irradiation system 20, an electron beam irradiation system 30, an argon ion beam irradiation system 40, nanotweezers 50 (microtweezers), a sample stage 60, a secondary charged particle detector 70, and a gas gun 80. The pressure in the vacuum chamber 10 can be reduced to a predetermined vacuum. All of the above-mentioned components are totally or in part disposed in the vacuum chamber 10.

The ion beam irradiation system 20 includes an ion source 21 for generating ions and an ion optical system 22 for forming a focused ion beam from ions which flow out of the ion source 21 and for scanning with the focused ion beam. A sample body Wa placed on the sample stage 60 disposed in the vacuum chamber 10 is irradiated with an ion beam 20A which is a charged particle beam from the ion beam irradiation system 20 provided with an ion beam body tube 23. Here, secondary charged particles such as secondary ions or secondary electrons are generated from the sample body Wa. These secondary charged particles are detected by the secondary charged particle detector 70 to acquire an image of the sample body Wa. Further, by increasing the strength of the ion beam 20A, the ion beam irradiation system 20 can also etch the sample body Wa in the range of the irradiation.

The ion optical system 22 is adapted to include, for example, a condenser lens for condensing the ion beam 20A, a diaphragm for narrowing the ion beam 20A, an aligner for adjusting an axis of the ion beam 20A, an objective lens for condensing the ion beam 20A onto the sample, and a deflector for scanning the sample with the ion beam 20A.

The electron beam irradiation system 30 includes an electron source 31 for emitting electrons and an electron optical system 32 for forming a beam from electrons emitted from the electron source 31 and for scanning with the electron beam. By irradiating the sample body Wa with an electron beam 30A ejected from the electron beam irradiation system 30, secondary electrons are generated from the sample body Wa. The generated secondary electrons are detected by the secondary charged particle detector 70 to acquire an image of the sample body Wa. Here, the portion of the sample body Wa irradiated with the electron beam 30A ejected from an electron beam body tube 33 is the same portion as that of the sample body Wa irradiated with the ion beam 20A. It is to be noted that, in the method of preparing a transmission electron microscope sample according to the present invention, a charged particle beam system which does not include the electron beam irradiation system 30 may also be used.

Similarly to the ion beam irradiation system 20, the argon ion beam irradiation system 40 includes an argon ion source 41, an argon ion optical system 42, an argon ion beam body tube 43, and further, a beam position control means 44 for controlling the irradiation position of an argon ion beam. An argon ion beam for cleaning a finished surface Wb1 of a sample piece (sample piece for transmission electron microscope) Wb to be described below is irradiated from the argon ion beam irradiation system 40 with the position thereof being controlled by the beam position control means 44. It is to be noted that, in the method of preparing a transmission electron microscope sample according to the present invention, a charged particle beam system which does not include the argon ion beam irradiation system 40 may also be used.

The sample stage 60 movably supports a sample table 61. The sample body Wa (for example, semiconductor wafer) and a sample holder 62 for fixing the sample piece Wb prepared from the sample body Wa are fixed onto the sample table 61. The sample stage 60 can change the position of the sample table 61 on five axes. More specifically, the sample stage 60 is adapted to have an XYZ moving mechanism 60b for moving the sample table 61 along an X axis and a Y axis which are in parallel to a horizontal plane and which are orthogonal to each other and along a Z axis which is orthogonal to the X axis and the Y axis, a rotation mechanism 60c for rotating the sample table 61 about the Z axis, and a tilt mechanism 60a for rotating the sample table 61 about the X axis (or the Y axis). By changing the position of the sample table 61 on the five axes, the sample stage 60 is adapted to move a specific portion of the sample body Wa to a position irradiated with the ion beam 20A.

The pressure in the vacuum chamber 10 can be reduced to a predetermined vacuum. The sample table 61, the nanotweezers 50, the secondary charged particle detector 70, and the gas gun 80 are provided in the vacuum chamber 10.

The nanotweezers 50 is held by a tweezers holder 52. The tweezers holder 52 can change the position of the nanotweezers 50 on five axes with a tweezers stage 51. More specifically, the tweezers stage 51 is adapted to have an XYZ moving mechanism 51b for moving the tweezers holder 52 along an X axis and a Y axis which are in parallel to the horizontal plane and which are orthogonal to each other and along a Z axis which is orthogonal to the X axis and the Y axis, a rotation mechanism 51c for rotating the tweezers holder 52 about the Z axis, and a tilt mechanism 51 for rotating the tweezers holder 52 about the X axis (or the Y axis). Tip portions of the nanotweezers 50 can be operated to be opened and closed by a pinch mechanism 53 for making the nanotweezers 50 pinch.

The secondary charged particle detector 70 detects secondary electrons or secondary ions generated from the sample body Wa when the sample body Wa is irradiated with the ion beam 20A or the electron beam 30A from the ion beam irradiation system 20 or the electron beam irradiation system 30.

The gas gun 80 emits a predetermined gas such as an etching gas to the sample body Wa. By irradiating the sample body Wa with the ion beam 20A with the etching gas being supplied from the gas gun 80, the etching rate of the sample with the ion beam 20A can be made higher.

The charged particle beam system 100 includes a control portion 90 for controlling portions forming the system. The control portion 90 is connected to the ion beam irradiation system 20, the electron beam irradiation system 30, the argon ion beam irradiation system 40, the nanotweezers 50, the secondary charged particle detector 70, and the sample stage 60. The charged particle beam system 100 further includes a display device 91 for displaying a sample image acquired based on a signal detected by the secondary charged particle detector 70.

The control portion 90 comprehensively controls the charged particle beam system 100, and, converts the secondary charged particles detected by the secondary charged particle detector 70 into a luminance signal to generate image data and forms an image based on the generated image data to be output to the display device 91. This makes it possible for the display device 91 to display an observation image or a reference image of the sample as described in the above.

The control portion 90 also drives the sample stage 60 based on a command of a software or input by an operator to adjust the position and the attitude of the sample body Wa. This makes it possible to adjust the irradiation location and the irradiation angle on the surface of the sample with the ion beam 20A. For example, the sample stage 60 can be driven in synchronization with switching operation between the ion beam irradiation system 20 and the electron beam irradiation system 30 such that the sample body Wa is moved or tilted.

Further, the control portion 90 drives the tweezers stage 51 and the pinch mechanism 53 as well as the sample stage 60 to adjust the position and the attitude of the nanotweezers 50. This makes it possible to adjust the grab location, the grab angle, and the grab timing of the nanotweezers 50.

Figure 3:
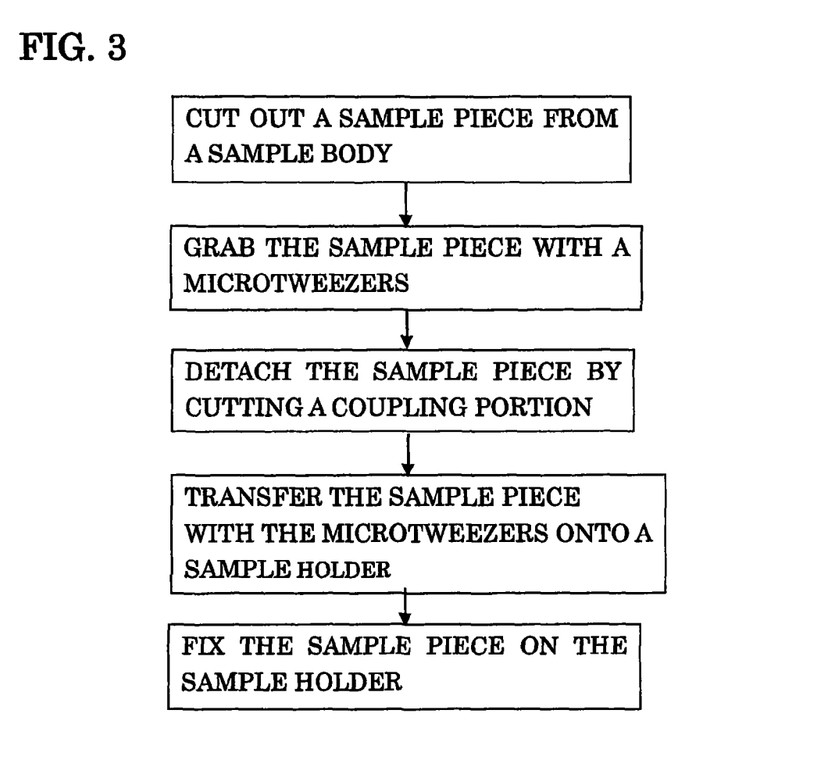
FIG. 3 shows a flow chart illustrating an order of operation in the embodiment of the present invention.
Figure 4:
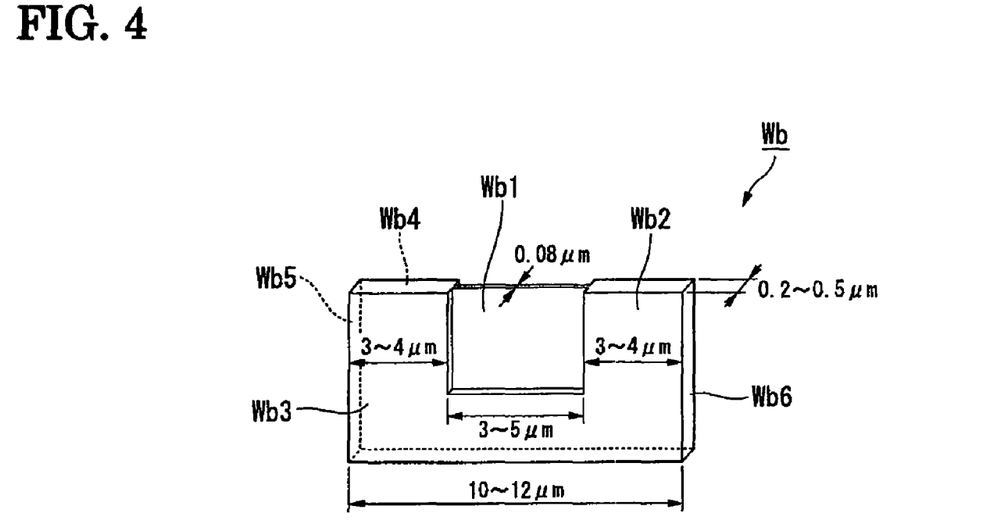
FIG. 4 shows a perspective view of a sample piece prepared in the embodiment of the present invention.

Next, the method of preparing a transmission electron microscope sample according to the present invention using the above-mentioned charged particle beam system 100 is described. FIG. 3 is a flow chart illustrating the order of operation in an embodiment of the method of preparing a transmission electron microscope sample according to the present invention. FIG. 4 is a perspective view of the sample piece Wb prepared in the embodiment of the method of preparing a transmission electron microscope sample according to the present invention. By processing the sample body Wa in accordance with the order of operation illustrated in FIG. 3, the sample piece Wb illustrated in FIG. 4 can be prepared. The sample piece Wb prepared according to the present invention is formed of, for example, a rectangular finished surface Wb1 having a longitudinal length of 3-5 μm and a thickness of 0.08 μm and a grabbing portion Wb2 which is in contact with three sides of the finished surface Wb1 and which is not in contact with the remaining one side of the finished surface Wb1 and having a thickness of 0.2-0.5 μm. The grabbing portion Wb2 includes a pair of first side surfaces Wb3 and Wb4 which are substantially in parallel with the finished surface Wb1 and a pair of second side surfaces Wb5 and Wb6 which are side surfaces adjoining to the first side surfaces. The longitudinal length of the first side surface Wb3 is, for example, 10-12 μm. The finished surface Wb1 is provided at a position sandwiched between the pair of first side surfaces Wb3 and Wb4 substantially in parallel to the first side surfaces so as to form a step portion with respect to the grabbing portion Wb2. It is to be noted that the dimensions of the sample piece is not limited to those of the sample piece Wb illustrated in FIG. 4.

Further, the difference in thickness between the finished surface Wb1 and the grabbing portion Wb2 in the sample piece Wb illustrated in FIG. 4 is exaggerated in the sample piece Wb illustrated in figures referred to in the following for the sake of simplicity of the description.

Figure 5:
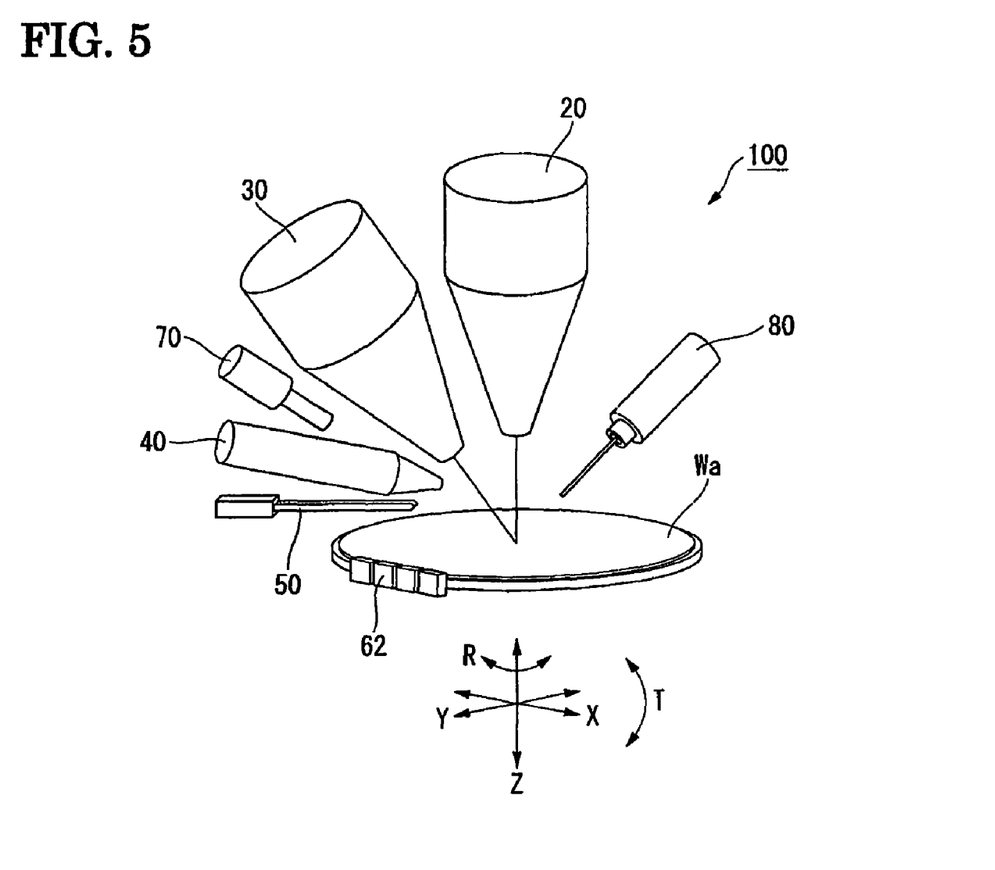
FIG. 5 shows a schematic perspective view around a sample body in the charged particle beam system used in the embodiment of the present invention before a sample is prepared.
Figure 6:
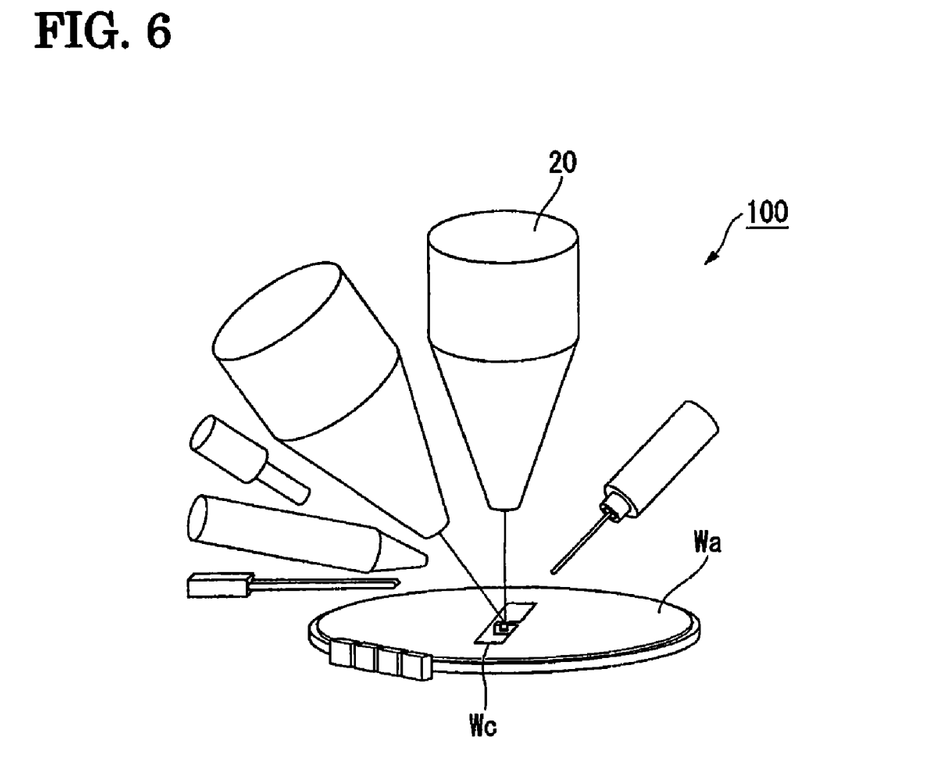
FIG. 6 shows a schematic perspective view around the sample body in the charged particle beam system used in the embodiment of the present invention when a first step ends.

FIG. 5 is a schematic perspective view around the sample body Wa in the charged particle beam system 100 before the sample is prepared. FIG. 6 is a schematic perspective view around the sample body Wa in the charged particle beam system 100 when a first step ends. As the first step, based on a command of a software or input by an operator, the control portion 90 carries out digging processing by etching a substantially rectangular portion to be processed Wc on both sides of a portion to be the sample piece Wb of the sample body Wa by the ion beam irradiation system 20 while driving the sample stage 60 on the five axes to form a thin piece portion Wb0. The detail is described in the following.

Figure 7:
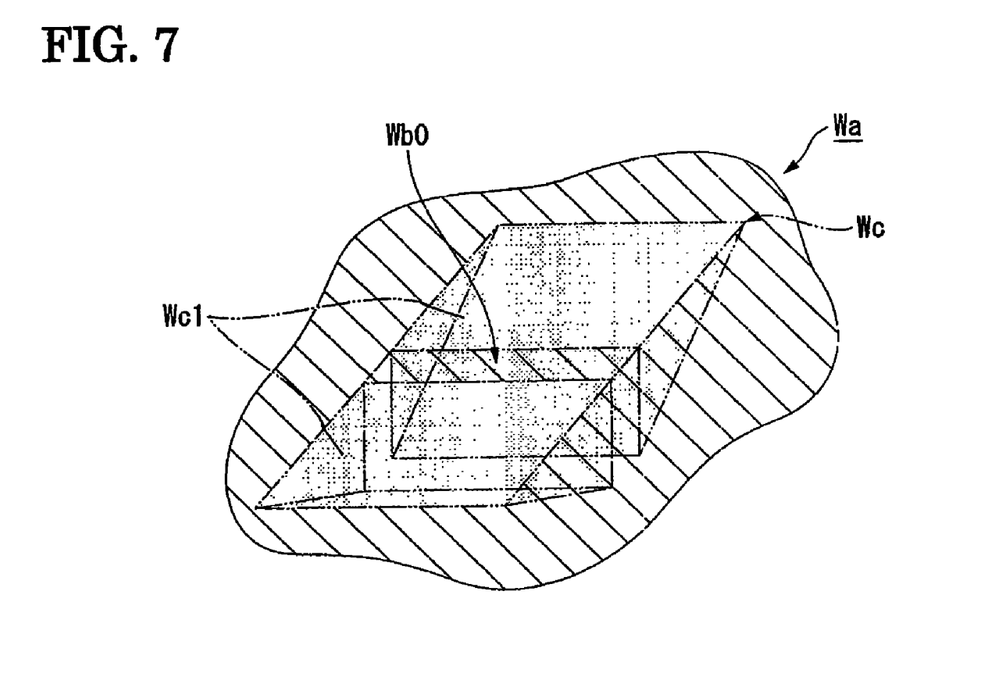
FIG. 7 shows a perspective view in a process of the first step around a portion to be processed of the sample body in the charged particle beam system used in the embodiment of the present invention.

FIG. 7 to FIG. 10 are perspective views in the process of the first step of processing a rectangular portion to be processed Wc1 of the sample body Wa processed using the charged particle beam system 100 to form the thin piece portion Wb0. The first step is described more specifically in the following. First, as illustrated in FIG. 7, in order to cut out the pair of first side surfaces Wb3 and Wb4 of the thin piece portion Wb0, the ion beam 20A is irradiated in a direction in parallel to the first side surfaces and the digging processing by etching is carried out such that the depth becomes gradually larger from an end of the portion to be processed Wc1 to the first side surfaces.

Figure 8:
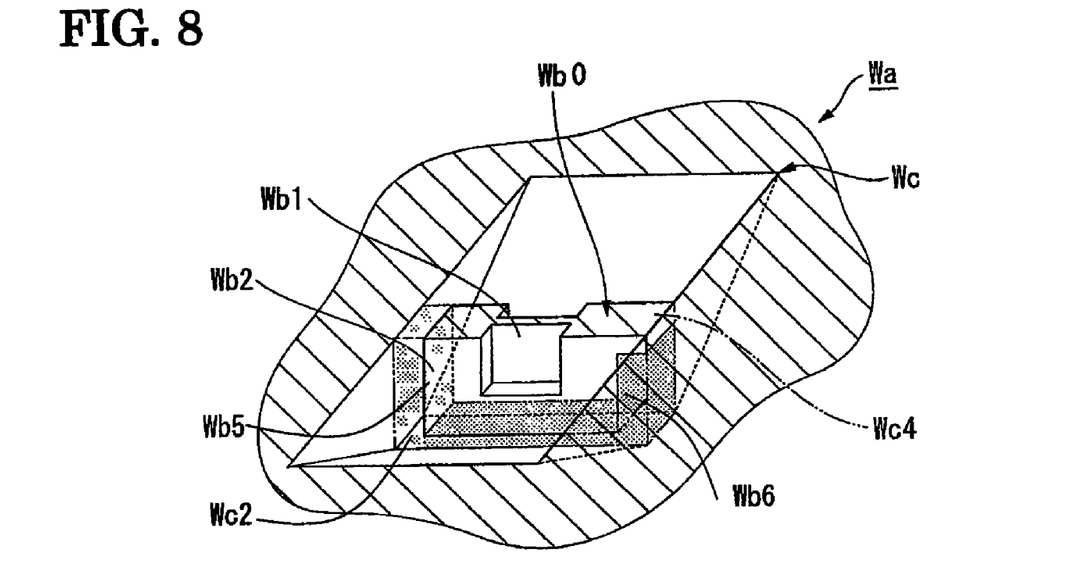
FIG. 8 shows a perspective view in the process of the first step around the portion to be processed of the sample body in the charged particle beam system used in the embodiment of the present invention.

Then, as illustrated in FIG. 8, in order to cut out the side surface Wb5 which is one of the second side surfaces of the thin piece portion Wb0, a Wb0 bottom portion, and the side surface Wb6 which is the other of the second side surfaces of the thin piece portion Wb0 with a coupling portion Wc4 for coupling the sample piece Wb and the sample body Wa being remained, the control portion 90 sets a portion to be processed Wc2 at a portion coupling the sample body Wa and a thin piece portion Wb0 side portion, a portion coupling the sample body Wa and a thin piece portion Wb0 bottom portion, and a part of another portion coupling the sample body Wa and a thin piece portion Wb0 side portion. By irradiating the portion to be processed Wc2 with the ion beam 20A to carry out etching processing, the coupling portions are cut. The processing of the Wc2 is carried out by irradiating the ion beam with the sample table 61 being tilted to tilt the sample.

Figure 9:
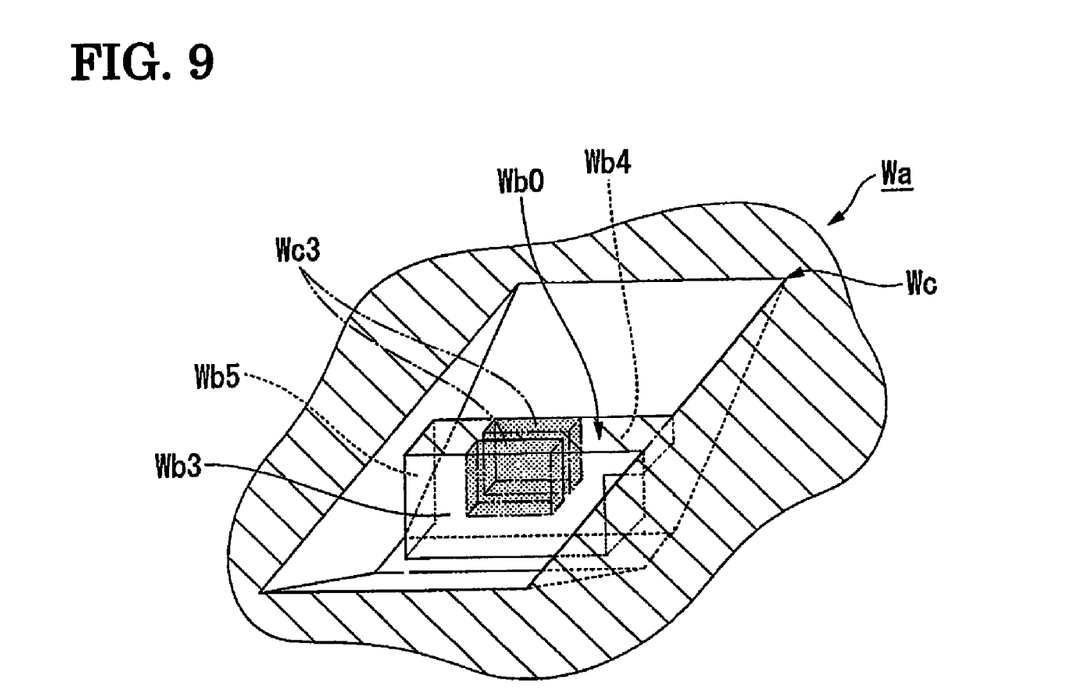
FIG. 9 shows a perspective view in the process of the first step around the portion to be processed of the sample body in the charged particle beam system used in the embodiment of the present invention.

Finally, the sample table is put back into its horizontal position, and, as illustrated in FIG. 9, in order to cut out the finished surface Wb1 by etching both sides of a center portion of the thin piece portion Wb0 and further thinning the thin piece portion Wb0, the control portion 90 sets two rectangular portions to be processed Wc3 on both upper sides of the thin piece portion from the pair of first side surfaces Wb3 and Wb4 to the finished surface Wb1 of the thin piece portion Wb0. The ion beam is made to scan the portions to be processed Wc3 from above to carry out removing processing to form the finished surface Wb1 on both sides of the thin piece portion.

Figure 10:
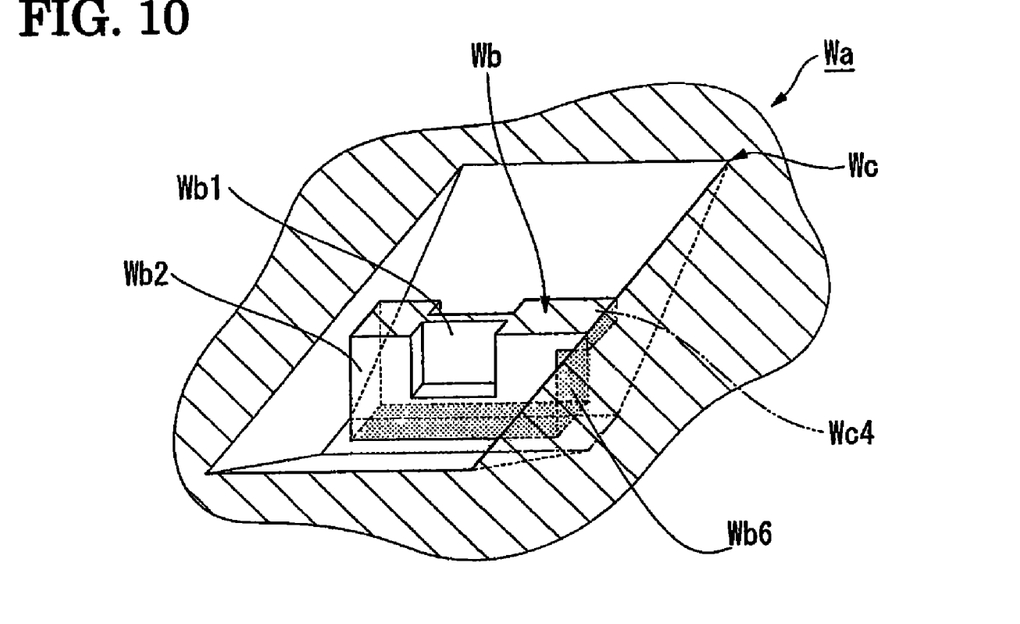
FIG. 10 shows a perspective view in the process of the first step around the portion to be processed of the sample body in the charged particle beam system used in the embodiment of the present invention.

In carrying out the first step, as illustrated in FIG. 10, the control portion 90 cuts out the sample piece Wb having the finished surface Wb1 and the grabbing portion Wb2 which is thicker than the finished surface Wb1 and the coupling portion Wc4 for coupling the sample piece Wb and the sample body Wa by carrying out etching processing of the portions to be processed Wc1 to Wc3 in the portion to be processed Wc of the sample body Wa to carry out processing to form the thin piece by digging grooves and to cut and finish the thin piece. The coupling portion Wc4 couples the side surface Wb6 which is one of the second side surfaces of the sample piece Wb and the sample body Wa. It is to be noted that the order of processing of the portions to be processed Wc2 and Wc3 in the first step is not specially limited. However, it is preferable that the processing of removing the portions to be processed Wc3 to cut out the finished surface Wb1 be the last in the first step in order to make as small as possible the influence of the ion beam 20A on the finished surface Wb1 during other portions to be processed are processed.

Figure 11:
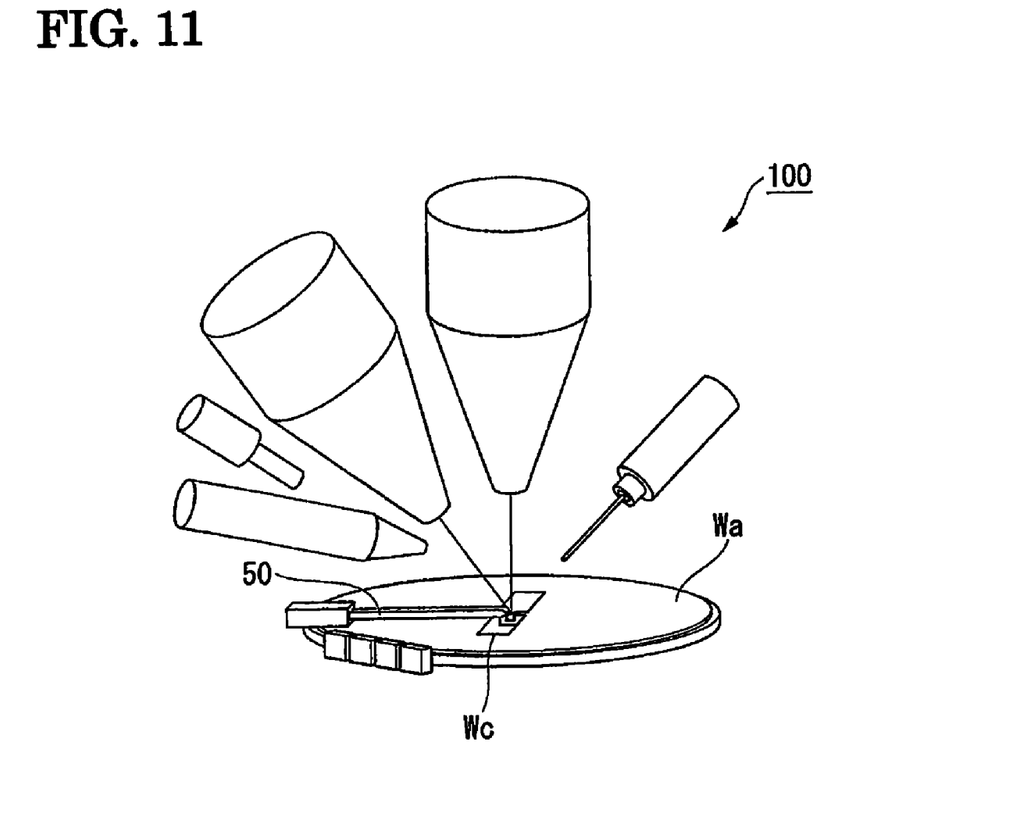
FIG. 11 shows a schematic perspective view around the sample body in the charged particle beam system used in the embodiment of the present invention when a second step ends.

FIG. 11 is a schematic perspective view around the sample body Wa in the charged particle beam system 100 when a second step ends. As the second step, the control portion 90 makes the grabbing portion Wb2 which is a thick portion of the sample piece Wb pinched by the nanotweezers 50 with the finished surface Wb1 of the sample piece Wb which is cut out in the first step being covered with the nanotweezers 50 by moving the nanotweezers 50 serving as a grabbing member and making the nanotweezers 50 pinch.

Figure 12:
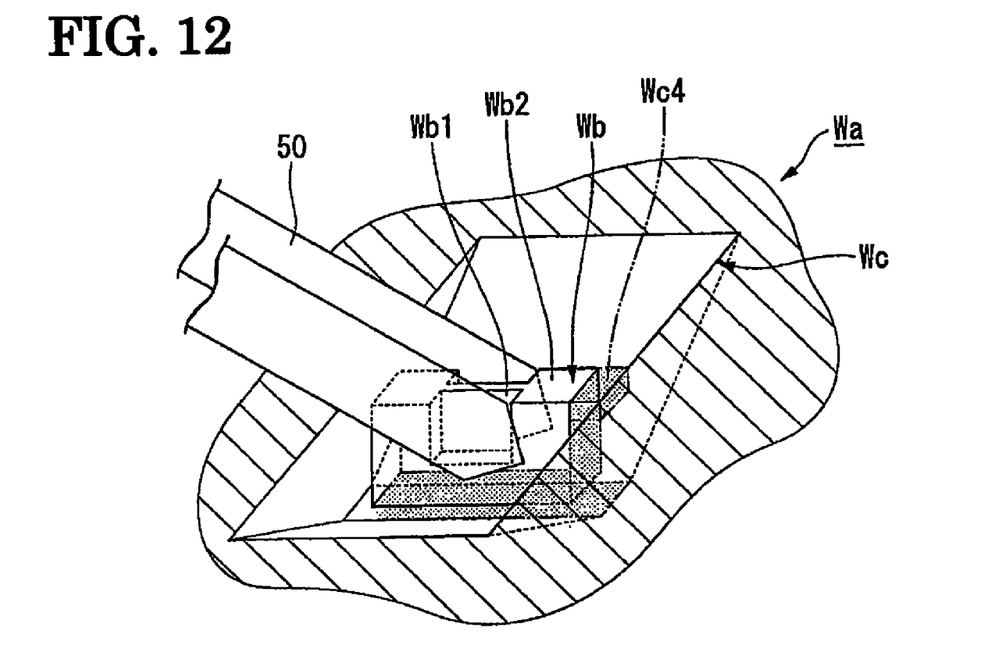
FIG. 12 shows a perspective view around the portion to be processed of the sample in the charged particle beam system used in the embodiment of the present invention when the second step ends.

FIG. 12 is a perspective view around the portion to be processed Wc of the sample body Wa in the charged particle beam system 100 when the second step ends. The second step is described more specifically in the following. First, the control portion 90 makes the nanotweezers 50 go toward the sample piece Wb from a direction in which the processing of cutting the portion to be processed Wc2 is carried out in the first step to cover the finished surface Wb1 of the sample piece Wb by driving the XYZ moving mechanism 51b, the rotation mechanism 51c, and the tilt mechanism 51a of the tweezers stage 51. Then, the control portion 90 makes the grabbing portion Wb2 of the sample piece Wb pinched by driving the pinch mechanism 53 of the nanotweezers 50. Because the thickness of the grabbing portion Wb2 is thicker at both sides than the thin piece portion in which the finished surface Wb1 is formed, the nanotweezers 50 do not contact the finished surface Wb1. Therefore, the finished surface Wb1 is not damaged.

Figure 13:
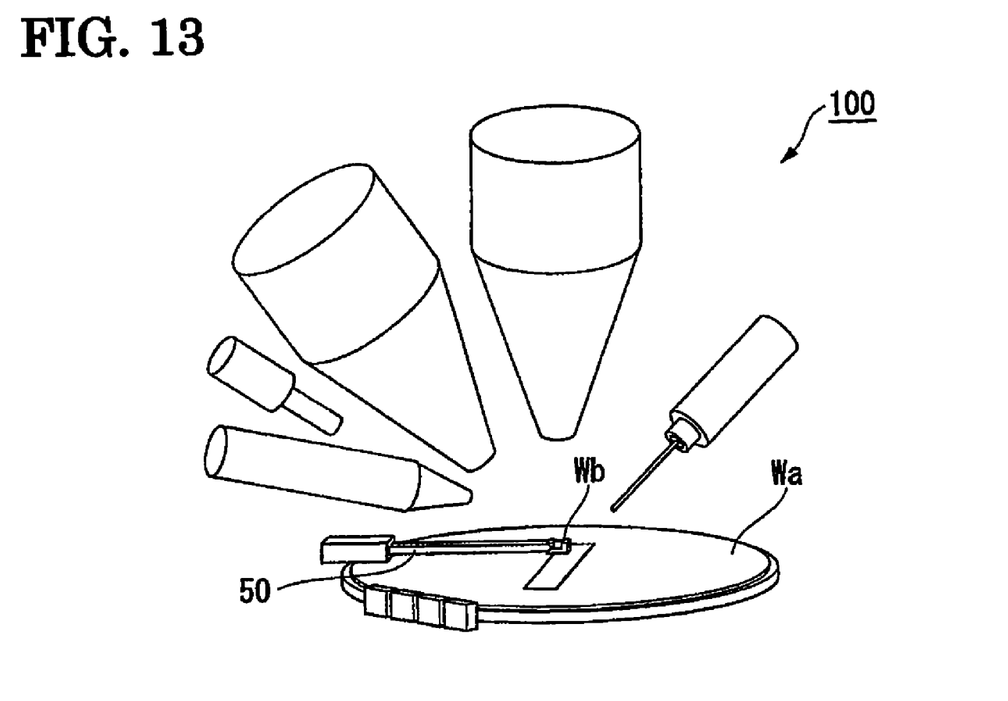
FIG. 13 shows a schematic perspective view around the sample body in the charged particle beam system used in the embodiment of the present invention when a third step ends.

FIG. 13 is a schematic perspective view around the sample body Wa in the charged particle beam system 100 when a third step ends. As the third step, the control portion 90 drives the sample stage 60 based on a command of a software or input by an operator to dispose the sample at a predetermined position, and after that, makes the coupling portion Wc4 cut by scanning of the ion beam from the ion beam irradiation system 20 to detach the sample piece Wb pinched by the nanotweezers 50 in the second step from the sample body Wa.

Figure 14:
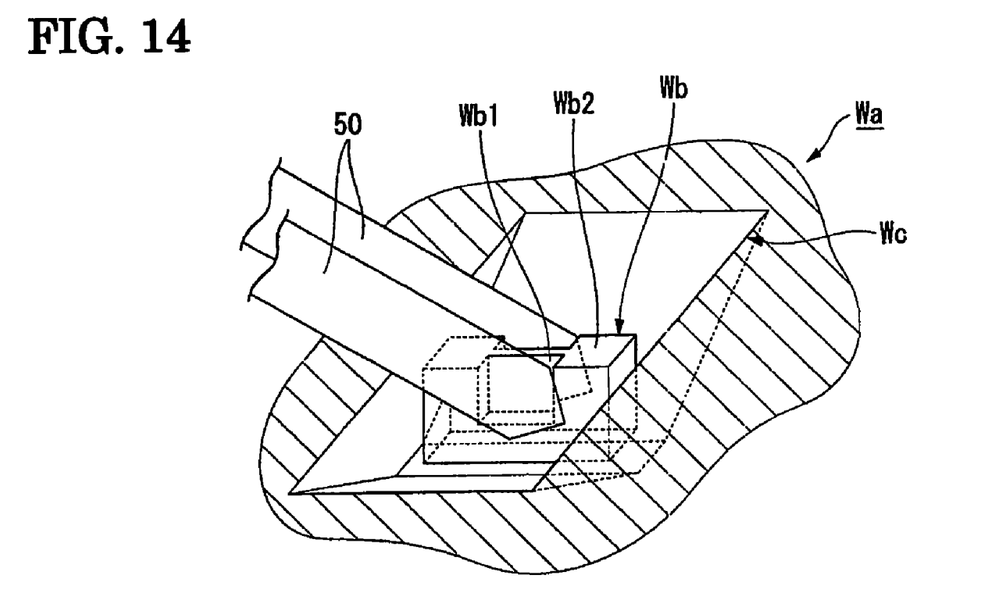
FIG. 14 shows a perspective view around the portion to be processed of the sample in the charged particle beam system used in the embodiment of the present invention when the third step ends.

FIG. 14 is a perspective view around the portion to be processed Wc of the sample body Wa in the charged particle beam system 100 when the third step ends. The third step is described more specifically in the following. In FIG. 12, the control portion 90 drives the sample stage 60 based on a command of a software or input by an operator to dispose the sample at a predetermined position, and after that, a slitting processing of the coupling portion Wc4 for coupling the sample piece Wb and the sample body Wa is carried out to cut the coupling portion Wc4 and detach the sample piece Wb by scanning of the ion beam from the ion beam irradiation system 20. Here, the coupling portion Wc4 is cut in the slitting processing in which the ion beam is irradiated. However, in this case, because the sample piece Wb1 is pinched by the nanotweezers 50 and the finished surface Wb1 is covered with the nanotweezers 50, damage by the ion beam is less liable to occur, and readhesion by the ion beam etching can be reduced.

Figure 15:
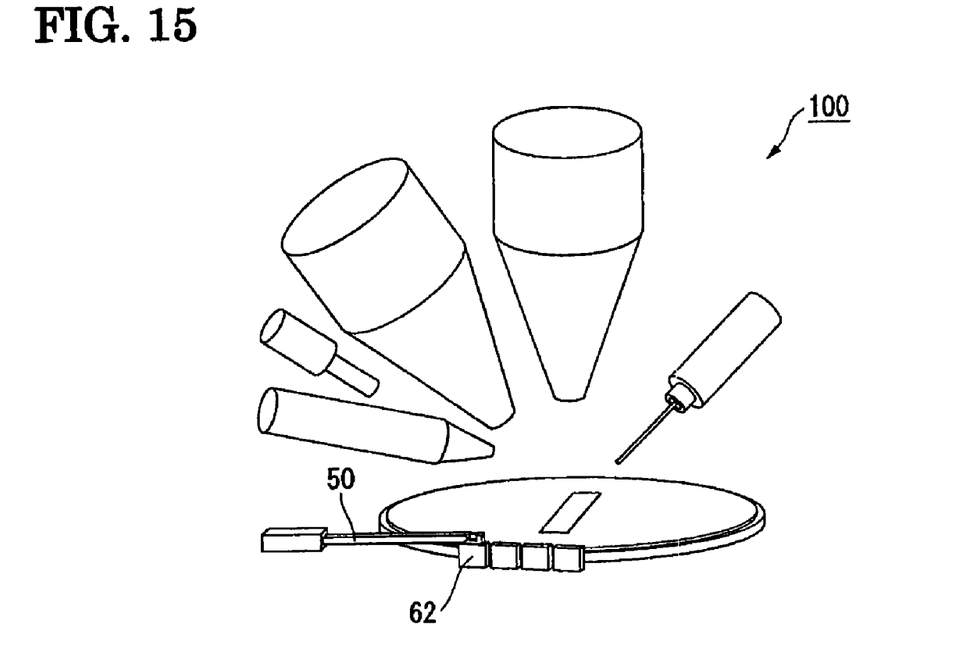
FIG. 15 shows a schematic perspective view around the sample body in the charged particle beam system used in the embodiment of the present invention when a fourth step ends.

FIG. 15 is a schematic perspective view around the sample body Wa in the charged particle beam system 100 when a fourth step ends. As the fourth step, the control portion 90 transfers and fixes the sample piece Wb pinched by the nanotweezers 50 onto a predetermined sample holder 62 by moving the nanotweezers 50.

Figure 16:
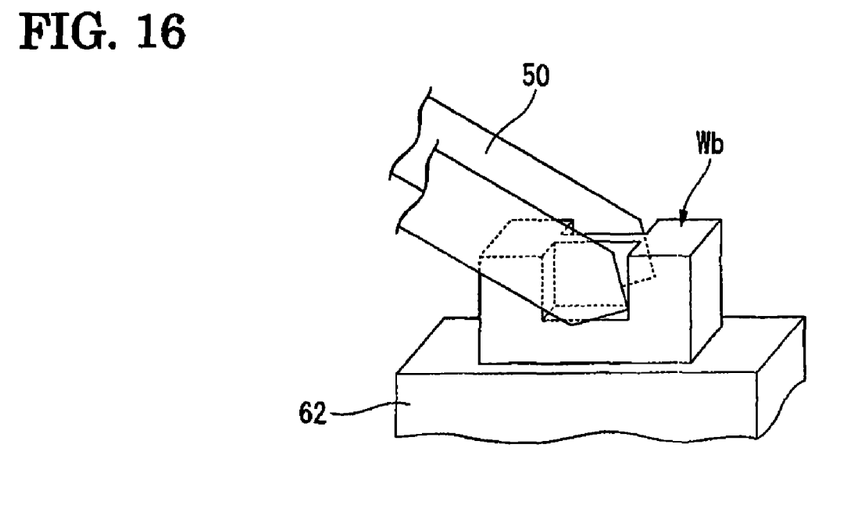
FIG. 16 shows a perspective view around the portion to be processed of the sample in the charged particle beam system used in the embodiment of the present invention when the fourth step ends.

FIG. 16 is a perspective view around the portion to be processed Wc of the sample body Wa in the charged particle beam system 100 when the fourth step ends. The fourth step is described more specifically in the following. The control portion 90 moves the nanotweezers 50 which pinches the sample piece Wb to a predetermined position on the sample holder 62 by driving the XYZ moving mechanism 51b, the rotation mechanism 51c, and the tilt mechanism 51a of the tweezers stage 51, and fixes the sample piece Wb onto the sample holder 62 by driving the pinch mechanism 53.

Figure 17:
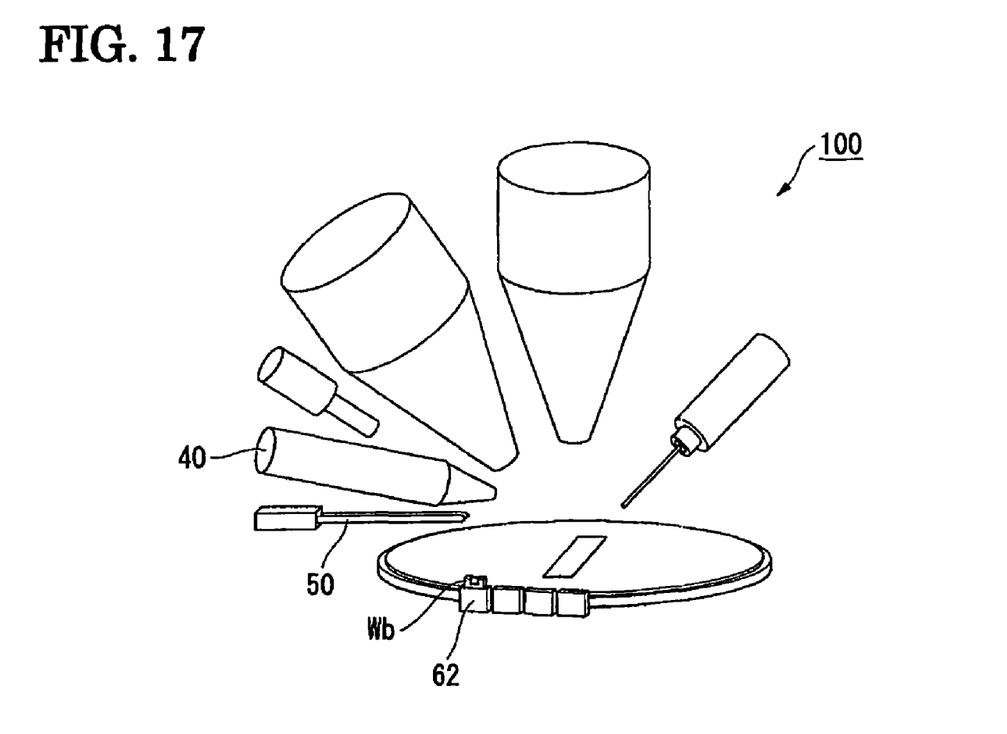
FIG. 17 shows a schematic perspective view around the sample body in the charged particle beam system used in the embodiment of the present invention after the sample is fixed.

FIG. 17 is a schematic perspective view around the sample body Wa in the charged particle beam system 100 after the sample is fixed. The control portion 90 ends the series of steps for preparing the sample by returning the nanotweezers 50 to its home position. It is to be noted that the nanotweezers 50 is not necessarily required to be returned to its home position. Further, as necessary, the surface of the sample piece Wb may be cleaned by the argon ion beam from the argon ion beam irradiation system 40.

According to the above, because, in the second step, the finished surface Wb1 of the sample piece Wb is covered with the nanotweezers 50, contamination does not occur on the finished surface Wb1 by the ion beam 20A in the cutting processing by etching of the coupling portion Wc4 for coupling the sample piece Wb and the sample body Wa by irradiating the ion beam 20A in the third step. Further, particles generated in the etching do not adhere.

Although an embodiment of the present invention is described in detail in the above with reference to the drawings, the specific structure thereof is not limited to the embodiment, and design changes within the gist of the present invention also fall within the scope of the present invention.

Figure 18:
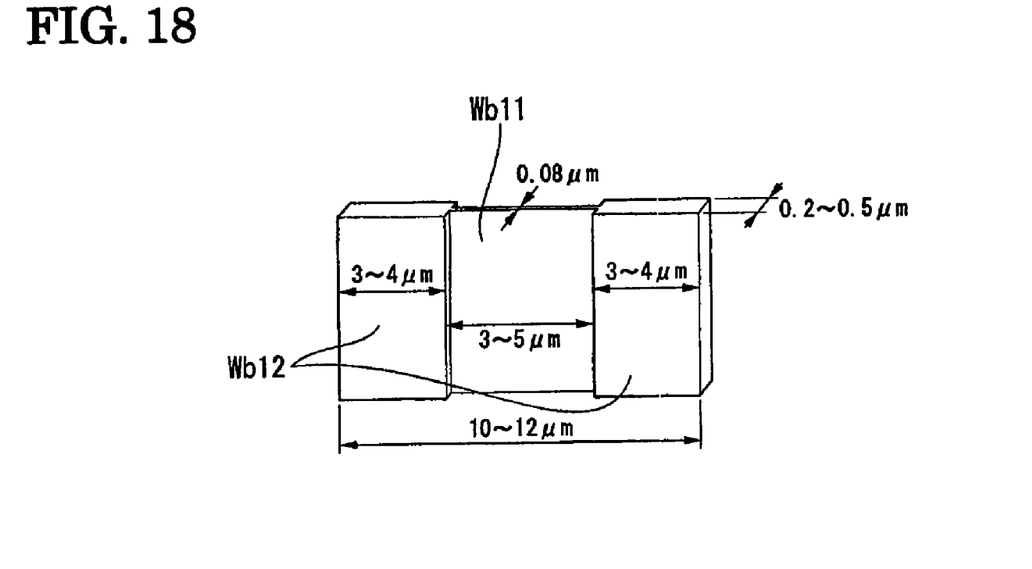
FIG. 18 shows a perspective view of a sample piece which can be prepared by the method of preparing a transmission electron microscope sample according to the present invention.

For example, the shape of the sample piece prepared by the method of preparing a transmission electron microscope sample according to the present invention is not limited to the one illustrated in FIG. 4. FIG. 18 is a perspective view of a sample piece which can be prepared by the method of preparing a transmission electron microscope sample according to the present invention. The sample piece is different from the sample piece Wb illustrated in FIG. 4 in that a finished surface Wb11 of the sample piece illustrated in FIG. 18 runs vertically all the way along the side surfaces of the sample piece. In the sample piece illustrated in FIG. 18, because the nanotweezers 50 grab a grabbing portion Wb12 which is thicker than the finished surface Wb11 with an upper portion of the finished surface Wb11 being covered with the nanotweezers 50, contamination does not occur on the upper portion of the finished surface Wb 11. Further, because the nanotweezers do not contact the finished surface Wb 11, the finished surface Wb11 is not damaged. Therefore, also with regard to the sample piece having the shape illustrated in FIG. 18, the finished surface Wb11 can be processed with the sample piece being coupled to the sample body Wa. In this way, insofar as there is a grabbing portion which is thicker than a finished surface, the shape of the sample piece which is prepared by the method of preparing a transmission electron microscope sample according to the present invention is not limited.

Further, the sample piece prepared by the method of preparing a transmission electron microscope sample according to the present invention is not necessarily required to have the grabbing portion which is thicker than the finished surface, and that the nanotweezers 50 does not directly contact the portion to be observed of the finished surface is sufficient. For example, a method in which a recessed portion is provided in the nanotweezers 50 and the nanotweezers 50 pinch the sample piece such that the portion to be observed of the finished surface is within the recessed portion of the nanotweezers 50, a method in which nanotweezers 50 additionally having a mechanism for covering the finished surface is used and covering the finished surface and grabbing the grabbing portion are carried out in parallel by different mechanisms, and the like are possible. However, in all of the methods, it takes time to accurately cover the portion to be observed of the finished surface, and thus, it is preferable to provide the thick grabbing portion around the finished surface.

Further, the shapes of the portions to be processed Wc1 to Wc3 described in the first step are not limited thereto, and it is sufficient that the portion to be the sample piece Wb can be grabbed. For example, the depth of the cutting processing of the portion to be processed Wc1 is not specially limited insofar as the finished surface Wb11 of the sample piece Wb is covered with the nanotweezers 50 and the grabbing portion Wb2 of the sample piece Wb can be grabbed.

Further, in the second step, the nanotweezers 50 is not necessarily required to enter from the direction in which the cutting processing of the portion to be processed Wc2 is carried out (for example, the nanotweezers 50 may enter from immediately above the portion to be the sample piece Wb or from an opposite direction with respect to the portion to be processed Wc2 in the sample piece Wb). However, when, in the third step, the coupling portion Wc4 is covered from the ion beam 20A by the entrance of the nanotweezers 50, the productivity is decreased because the cutting processing of the coupling portion Wc4 is carried out with repeated adjustment of the position of the sample body Wa by the sample stage 60. Therefore, it is preferable that the nanotweezers 50 enter from the direction in which the cutting processing of the portion to be processed Wc2 is carried out.

Further, the coupling portion is not necessarily required to have the shape of Wc4 illustrated in this embodiment, and is not specially limited insofar as the positioning of the nanotweezers 50 can be carried out with the sample piece Wb being coupled to the sample body Wa. For example, the coupling portion may couple the sample piece Wb and the sample body Wa only on one surface, and not the entire surface but a part of the surface of the sample piece Wb may be coupled to the sample body Wa. Change in the shape of the coupling portion can be accommodated by changing the shape of the portion to be processed Wc2 in the first step.

Further, the method of grabbing with the nanotweezers 50 is not limited to pinching by the pinch mechanism 53, and, for example, the material, shape, and the like of the nanotweezers 50 may conform to a member of the sample body Wa and the grabbing may be carried out by physical adsorption.

What is claimed is:

1. A method of preparing a transmission electron microscope sample, a sample piece being detached with a charged particle beam from a sample body, the sample piece having a substantially planar finished surface which can be observed with a transmission electron microscope and a grabbing portion which microtweezers can grab without contacting the finished surface, and the sample piece being transferred with the microtweezers to be fixed onto a sample holder, the method comprising:
    a first step of cutting out the sample piece from the sample body with the charged particle beam with a coupling portion for coupling the sample piece to the sample body remaining;
    a second step of grabbing with the microtweezers the grabbing portion of the sample piece with a portion to be observed of the finished surface of the sample piece cut out in the first step being entirely covered with the microtweezers;
    a third step of detaching the sample piece grabbed with the microtweezers in the second step from the sample body by cutting the coupling portion with the charged particle beam with a grabbed state of the sample piece being maintained; and
    a fourth step of transferring and fixing the sample piece grabbed with the microtweezers and detached in the third step onto the sample holder.

2. The method of preparing a transmission electron microscope sample according to claim 1, wherein in the first step, the grabbing portion of the sample piece is processed such that a thickness of the grabbing portion is larger than a thickness of the finished surface.

3. The method of preparing a transmission electron microscope sample according to claim 1, wherein in the first step, after the grabbing portion of the sample piece is cut out, the finished surface of the sample piece is processed.

4. A method of preparing a transmission electron microscope sample, a sample piece being detached with a charged particle beam from a sample body, the sample piece having a substantially planar finished surface which can be observed with a transmission electron microscope and a grabbing portion which microtweezers can grab without contacting the finished surface, and the sample piece being transferred with the microtweezers to be fixed onto a sample holder, the method comprising:
    a first step of forming a thin piece portion including the grabbing portion and the finished surface by etching the sample body using the charged particle beam with a coupling portion for coupling the thin piece portion to the sample body remaining;
    a second step of grabbing with the microtweezers the grabbing portion of the thin piece portion with a portion to be observed of the finished surface of the thin piece portion formed in the first step being entirely covered with the microtweezers;
    a third step of detaching the thin piece portion grabbed with the microtweezers in the second step from the sample body by cutting the coupling portion with the charged particle beam with a grabbed state of the thin piece portion being maintained to form the sample piece for a transmission electron microscope; and
    a fourth step of grabbing with the microtweezers the sample piece for a transmission electron microscope detached in the third step to transfer and fix the sample piece for a transmission electron microscope onto the sample holder.

5. A method of preparing a transmission electron microscope sample, comprising:
    a first step of forming a thin piece portion by irradiating a focused ion beam from above a sample surface;
    a second step of tilting a sample table and cutting both ends of the thin piece portion and a bottom portion of the thin piece portion by irradiating the focused ion beam with a coupling portion remaining at any one end of the both ends;
    a third step of putting the sample table back into a horizontal position and further thinning a part of the thin piece portion by irradiating the beam to both sides of the thin piece portion to form a finished surface;
    a fourth step of grabbing a thick portion of the thin piece portion with a portion to be observed of the finished surface being entirely covered with a grabbing member;

a fifth step of cutting the coupling portion by irradiating the focused ion beam with a grabbed state of the thick portion in the fourth step being maintained to detach the thin piece portion from a sample body to form a thin piece; and a sixth step of transferring and fixing the thin piece detached in the fifth step onto a sample holder with the thick portion being grabbed by the grabbing member.

* * * * *